(12) United States Patent
Clark et al.

(10) Patent No.: US 7,022,708 B2
(45) Date of Patent: Apr. 4, 2006

(54) 4-PIPERAZINYL BENZENESULFONYL INDOLES AND USES THEREOF

(75) Inventors: Robin Douglas Clark, Lawai, HI (US); Ralph New Harris, III, Redwood City, CA (US); David Bruce Repke, Milpitas, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 224 days.

(21) Appl. No.: 10/687,091

(22) Filed: Oct. 16, 2003

(65) Prior Publication Data

US 2004/0087593 A1 May 6, 2004

Related U.S. Application Data

(60) Provisional application No. 60/419,369, filed on Oct. 18, 2002.

(51) Int. Cl.
*C07D 403/04* (2006.01)
*A61K 31/496* (2006.01)

(52) U.S. Cl. .................. 514/254.09; 544/373
(58) Field of Classification Search .......... 544/373; 514/254.09
See application file for complete search history.

(56) References Cited

U.S. PATENT DOCUMENTS

2004/0024210 A1 2/2004 Johanssen et al.

FOREIGN PATENT DOCUMENTS

| FR | 2 729 144 A1 | 7/1996 |
|---|---|---|
| WO | WO 93/03012 A1 | 2/1993 |
| WO | WO 98/27081 A1 | 6/1998 |
| WO | WO 99/02502 A2 | 1/1999 |
| WO | WO 00/58304 A1 | 10/2000 |
| WO | WO 01/64642 A2 | 9/2001 |
| WO | WO 03/104193 A1 | 12/2003 |

OTHER PUBLICATIONS

Robichaud et al. in Annual Reports in Medicinal Chemistry, vol. 36, p. 11-20 (2000).*
Rogers et al. Psychopharmacology, vol. 158, p. 114-119 (2001).*
Bromidge et al. Bioorganic & Medicinal Chemistry Letters, vol. 11, p. 55-58 (2001).*

* cited by examiner

*Primary Examiner*—Emily Bernhardt
(74) *Attorney, Agent, or Firm*—Robert C. Hall

(57) ABSTRACT

This invention relates to compounds which have generally 5-HT6 receptor affinity and which are represented by Formula I:

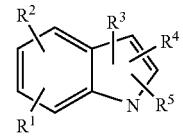

wherein $R^1$, $R^2$, $R^3$, $R^4$, and $R^5$ are as defined herein; or individual isomers, racemic or non-racemic mixtures of isomers, or pharmaceutically acceptable salts or solvates thereof. The invention further relates to pharmaceutical compositions containing such compounds, methods for their use as therapeutic agents, and methods of preparation thereof.

32 Claims, No Drawings

4-PIPERAZINYL BENZENESULFONYL INDOLES AND USES THEREOF

CROSS REFERENCE TO RELATED APPLCATION

This application is entitled under 35 USC §119(e) to the benefit of U.S. provisional application Ser. No. 60/419,369, filed Oct. 18, 2002, the disclosure of which is incorporated herein by reference in its entirety.

FIELD OF THE INVENTION

This invention relates to new 4-piperazinyl indole derivatives with 5-HT6 receptor affinity, and associated pharmaceutical compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nervous system disorders. In particular, 5-HT6 receptor selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine, and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. (See for ex. B. L. Roth et al., J. Pharmacol. Exp. Ther., 268, pages 1403–14120 (1994), D. R. Sibley et al., Mol. Pharmacol., 43, 320–327 (1993), A. J. Sleight et al, Neurotransmission, 11, 1–5 (1995), and A. J. Sleight et al. Serotonin ID Research Alert, 1997, 2 (3), 115–8). 5-HT6 antagonists have also been identified as potentially useful compounds for treatment of obesity. See for example, Bentley et al., *Br. J. Pharmac.* 1999, *Suppl* 126; Bently et al., *J. Psychopharmacol.* 1997, *Suppl A*64: 255; Wooley et al., *Neuropharmacology* 2001, 41: 210–129; and WO 02/098878.

SUMMARY

This invention relates to Compounds of the Formula I:

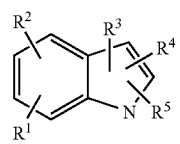

I wherein:

R$^1$ and R$^2$ each independently is hydrogen, alkyl, aryl, acyl, halo, nitro, amino, cyano, alkoxy, hydroxy, aryloxy, alkylthio, arylthio, thiol, carbonylamino, aminocarbonyl, or haloalkyl;

R$^3$ and R$^4$ each independently is hydrogen, halo, alkyl, acyl, aryl, or arylalkyl;

is R$^5$ is:

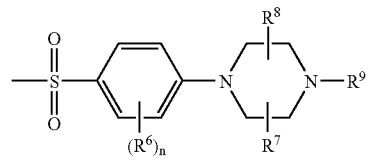

n is 0 to 4;

R$^6$ in each independent occurrence is hydrogen, alkyl, alkoxy, or halo;

R$^7$ and R$^8$ each independently is hydrogen or alkyl; and

R$^9$ is hydrogen, alkyl, or arylalkyl; or individual isomers, racemic or non racemic mixtures of isomers, prodrugs, or pharmaceutically acceptable salts or solvates thereof.

In another aspect, the invention relates to pharmaceutical compositions containing a therapeutically effective amount of at least one compound of Formula I, or individual isomers, racemic or non-racemic mixtures of isomers, or pharmaceutically acceptable salts or solvates thereof, in admixture with at least one suitable carrier.

In another aspect, this invention relates to a method of treatment of a disease in a mammal treatable by administration of a compound of Formula I having a selective affinity for the 5-HT6 receptor, in particular a method of treatment in a subject having a central nervous system (CNS) disease state, condition or disorder such as for example, Alzheimer's, psychoses, schizophrenia, manic depressions, neurological disorders, Parkinson's disease, amyotrophic lateral sclerosis, and Huntington's disease.

In another aspect, this invention relates to a method of treatment in a subject having a gastrointestinal disease such as irritable bowel syndrome (IBS).

In another aspect, there is provided a method for producing a compound of the invention comprising contacting a 4-halobenzenesulfonyl-indole of the Formula a:

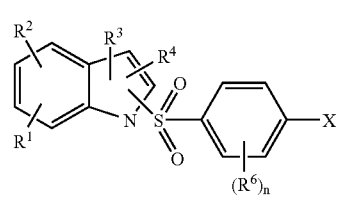

a wherein X is halo and n, R$^1$, R$^2$, R$^3$, R$^4$, and R$^6$ are as defined herein, with a piperazine of the Formula b:

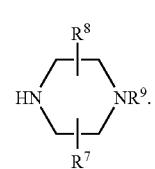

b to produce a compound of the Formula II:

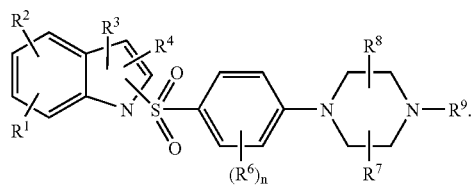

In another aspect, the invention further relates to a process which comprises: reacting or contacting a compound having the Formula c

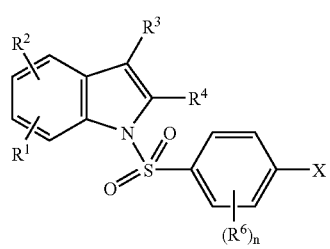

wherein X is halo and n, $R^1$, $R^2$, $R^3$, $R^4$, and $R^6$ are as defined herein, with a compound of Formula b:

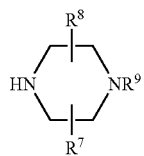

wherein $R^7$, $R^8$, and $R^9$ are as defined herein, to provide a compound of general Formula III:

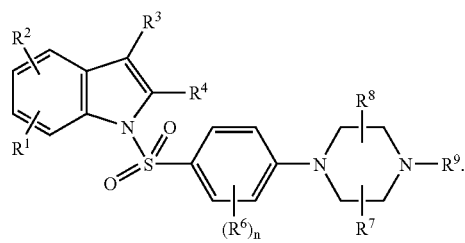

In another aspect, the invention relates a process which comprises: reacting or contacting a compound having the Formula d:

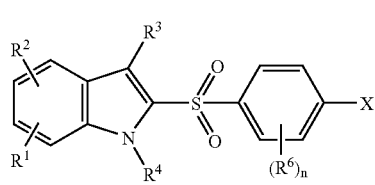

wherein X is halo and n, $R^1$, $R^2$, $R^3$, $R^4$, and $R^6$ are as defined herein, with a compound of Formula b:

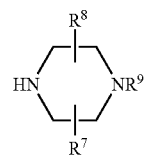

wherein $R^7$, $R^8$, and $R^9$ are as defined herein, to provide a compound of general Formula IV:

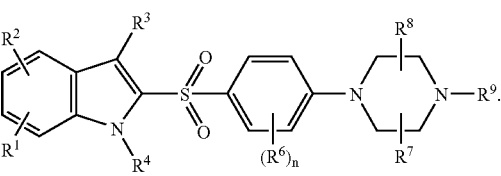

In still another aspect, the invention further provides a process which comprises: reacting or contacting a compound having a general Formula e:

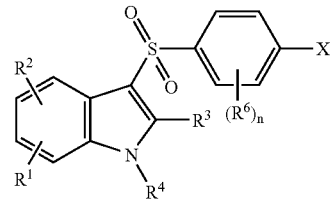

wherein X is halo and n, $R^1$, $R^2$, $R^3$, $R^4$, and $R^6$ are as defined herein, with a compound of Formula b:

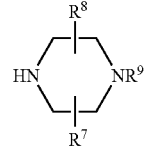

wherein $R^7$, $R^8$, and $R^9$ are as defined herein, to provide a compound of general Formula V:

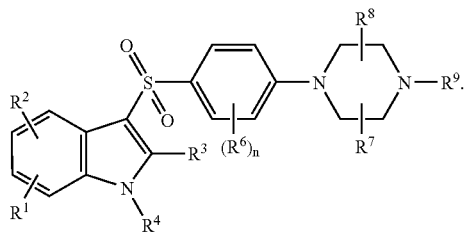

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear, branched, cyclic, or a combination of linear, branched, or cyclic saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, isobutyl, sec-butyl, tert-butyl, pentyl, n-hexyl, octyl, dodecyl, and the like.

"Lower alkyl" means the monovalent linear or branched saturated hydrocarbon radical, consisting solely of carbon and hydrogen atoms, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, and the like.

"Alkylene" means the divalent linear or branched saturated hydrocarbon radical, consisting solely of carbon and hydrogen atoms, having from one to six carbons inclusive, unless otherwise indicated. Examples of alkylene radicals include, but are not limited to, methylene, ethylene, propylene, 2-methyl-propylene, butylene, 2-ethylbutylene, and the like.

"Alkoxy" means the radical —O—R, wherein R is a lower alkyl radical as defined herein. Examples of alkoxy radicals include, but are not limited to, methoxy, ethoxy, isopropoxy, and the like.

"Halo", "halide" and "halogen", which may be used interchangeably, means fluoro, chloro, bromo, or iodo.

"Haloalkyl" means alkyl substituted with one or more same or different halo atoms, e.g., —CH$_2$Cl, —CF$_3$, —CH$_2$CF$_3$, —CH$_2$CCl$_3$, and the like.

"Alkylthio" or "alkylsulfanyl" means the radical —S—R, wherein R is a lower alkyl radical as defined herein. Examples of alkylthio radicals include, but are not limited to, methylthio, ethylthio, butylthio, and the like.

"Alkylsulfonyl" means the radical —SO$_2$R, wherein R is a lower alkyl radical as defined herein. Examples of alkylsulfonyl radicals include, but are not limited to, methylsulfonyl, ethylsulfonyl, and the like.

"Aryllthio" or "arylsulfanyl" means the radical —S—R, wherein R is an aryl radical as defined herein.

"Arylsulfonyl" means the radical —SO$_2$R, wherein R an aryl radical as defined herein.

"Aryl" means the monovalent cyclic aromatic hydrocarbon radical consisting of one or more fused rings in which at least one ring is aromatic in nature, which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like. Examples of substituted aryl radicals include but are not limited to fluorophenyl, chlorophenyl, dichlorophenyl, trifluoromethylphenyl, tolyl, and the like.

"Heteroaryl" means the monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of heteroaryl radicals include, but are not limited to, imidazolyl, oxazolyl, thiazolyl, pyrazinyl, thiophenyl, furanyl, pyranyl, pyridinyl, quinolinyl, isoquinolinyl, benzofuryl, benzothiophenyl, benzothiopyranyl, benzimidazolyl, benzooxazolyl, benzothiazolyl, benzopyranyl, indazolyl, indolyl, isoindolyl, naphtyridinyl, and the like.

"Leaving group" means the group with the meaning conventionally associated with it in synthetic organic chemistry, i.e., an atom or group displaceable under alkylating conditions. Examples of leaving groups include, but are not limited to, halogen, alkyl, or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Amino-protecting group" means the protecting group that refers to those organic groups intended to protect the nitrogen atom against undesirable reactions during synthetic procedures and includes, but is not limited to, benzyl (Bnz), benzyloxycarbonyl (carbobenzyloxy, Cbz), p-methoxybenzyloxycarbonyl, p-nitrobenzyloxycarbonyl, tert-butoxycarbonyl (Boc), trifluoroacetyl, and the like. It is preferred to use either Boc or Cbz as the amino-protecting group because of the relative ease of removal, for example by mild acids in the case of Boc, e.g., trifluoroacetic acid or hydrochloric acid in ethyl acetate or ethanol; or by catalytic hydrogenation in the case of Cbz.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, methyl or alkyl ethers, and the like. Protective or blocking groups for carboxyl groups are similar to those described for hydroxyl groups, preferably tert-butyl, benzyl, or methyl esters.

"Inert organic solvent" or "inert solvent" means the solvent is inert under the conditions of the reaction being described in conjunction therewith, including for example, benzene, toluene, acetonitrile (ACN), tetrahydrofuran (THF), N,N-dimethylformamide (DMF), chloroform, methylene chloride or dichloromethane (DCM), dichloroethane (DCE), diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate, and sodium hydroxide.

The preferred pharmaceutically acceptable salts are the salts formed from acetic acid, trifluoroacetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Prodrug" or "pro-drug" means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, sulfhydryl, carboxy, or carbonyl group in a compound of Formula I is bonded to any group that may be cleaved in vivo to regenerate the free hydroxyl, amino, sulfhydryl, carboxy, or carbonyl group respectively. Examples of prodrugs include, but are not limited to, esters (e.g. acetate, dialkylaminoacetates, formates, phosphates, sulfates, and benzoate derivatives), carbamates of hydroxy functional groups (e.g. N,N-dimethylcarbonyl), esters of carboxyl functional groups (e.g. ethyl esters and morpholinoethanol esters), N-acyl derivatives (e.g. N-acetyl), N-Mannich bases, Schiff bases, enaminones of amino functional groups, oximes, acetals, ketals, enol esters of ketones, aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp. 352–401; *Design of Prodrugs*, edited by H. Bundgaard, Elsevier Science, Amsterdam, 1985; *Design of Biopharmaceutical Properties through Prodrugs and Analogs*, Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

"Disease state" means any disease, condition, symptom, or indication.

Throughout the application the following abbreviations may be used with the following meaning:

Alk Alkyl group
Boc N-tert-butoxycarbonyl
m-CPBA m-Chloroperbenzoic acid
DCM Dichloromethane
DTB Di-tert-butyldicarbonate
DMF N,N-Dimethylformamide
DMFDMA N,N-dimethylformamide dimethyl acetal
DMSO Dimethylsulfoxide
L Leaving group
Oxone™ Potassium peroxymonosulfate
P Protective group
TFA Trifluoroacetic acid
THF Tetrahydrofuran Nomenclature The naming and numbering of the compounds of this invention is illustrated below:

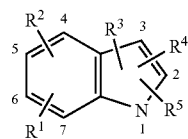

In general, the nomenclature used herein is based on AUTONOM™ v.4.0, a Beilstein Institute computerized system for the generation of IUPAC systematic nomenclature. However, because a strict adherence to these recommendations would result in the names changing substantially when only a single substituent is changed, compounds have been named in a manner that maintains consistency of nomenclature for the basic structure of the molecule. Any open valency on a nitrogen or oxygen molecule should be understood as indicating the presence of a hydrogen atom.

For example, a compound of Formula I wherein $R^2$, $R^3$ and $R^4$ are hydrogen, $R^1$ is fluorine (attached through the fifth position on the indole ring), $R^5$ is

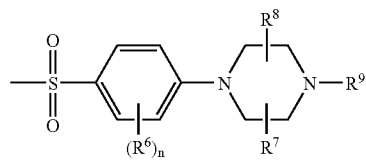

attached at the first position on the indole ring, $R^6$, $R^7$ and $R^8$ are hydrogen, and $R^9$ is methyl, is named 5-Fluoro-1-[4-(4-methyl-piperazin-1-yl)-benzenesulfonyl]-1H-indole.

Compounds and Compositions of the Invention

The invention provides Compounds of Formula I:

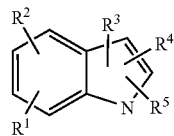

wherein:

$R^1$ and $R^2$ each independently is hydrogen, alkyl, aryl, acyl, halo, nitro, amino, cyano, alkoxy, hydroxy, aryloxy, alkylthio, arylthio, thiol, carbonylamino, aminocarbonyl, or haloalkyl; preferably $R^1$ and $R^2$ each independently is hydrogen, halo or alkoxy; more preferably hydrogen or halo;

$R^3$ and $R^4$ each independently is hydrogen, halo, alkyl, acyl, aryl, or arylalkyl; preferably $R^3$ and $R^4$ each independently is hydrogen or alkyl;

$R^5$ is:

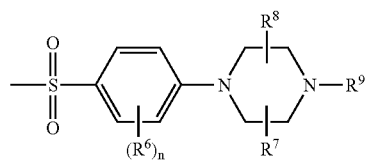

n is from 0 to 3; preferably n is 0 or 1;

$R^6$ in each occurrence independently is hydrogen, alkyl, alkoxy, or halo; preferably $R^6$ is hydrogen or halo;

$R^7$ and $R^8$ each independently is hydrogen or alkyl; and $R^9$ is hydrogen, alkyl, or arylalkyl; preferably $R^9$ is hydrogen or alkyl; or individual isomers, racemic or non racemic mixtures of isomers, prodrugs, or pharmaceutically acceptable salts or solvates thereof.

In certain embodiments of the invention, the Compounds of Formula I may be of Formula III:

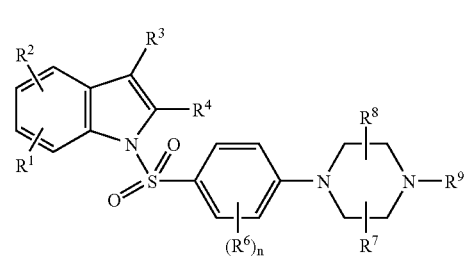

wherein n, $R^1$, $R^2$, $R^3$, $R^4$, $R^6$, $R^7$, $R^8$ and $R^9$ are as defined herein.

In other embodiments, Compounds of Formula I may be of Formula IV:

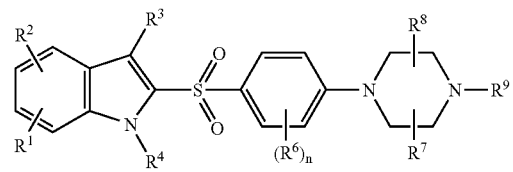

wherein n, $R^1$, $R^2$, $R^3$, $R^4$, $R^6$, $R^7$, $R^8$ and $R^9$ are as defined herein.

In more preferred embodiments, Compounds of Formula I are of the Formula V:

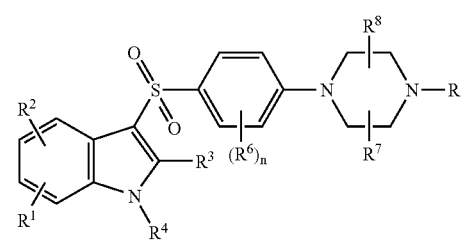

wherein n, $R^1$, $R^2$, $R^3$, $R^4$, $R^6$, $R^7$, $R^8$ and $R^9$ are as defined herein.

Representative compounds in accordance with the invention are shown in Table 1. In many instances the compounds in Table 1 are shown as hydrochloride salts.

TABLE 1

| # | STRUCTURE | M + H or MP ° C. | NAME | Example |
|---|---|---|---|---|
| 1 | 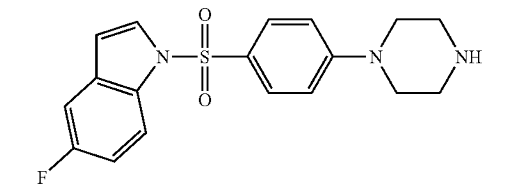 | M + H 360 | 5-Fluoro-1-(4-piperazin-1-yl-benzenesulfonyl)-1H-indole | 1 |
| 2 | 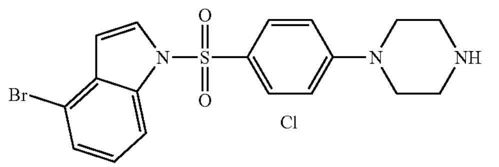 | M + H 421 | 4-Bromo-1-(4-piperazin-1-yl-benzenesulfonyl)-1H-indole | 1 |
| 3 | 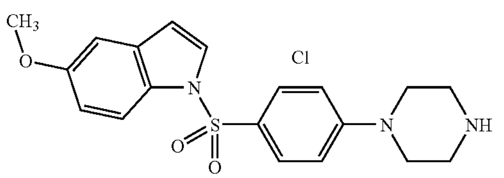 | M + H 372 | 5-Methoxy-1-(4-piperazin-1-yl-benzenesulfonyl)-1H-indole | 1 |
| 4 | 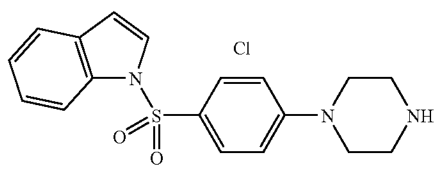 | M + H 342 | 1-(4-Piperazin-1-yl-benzenesulfonyl)-1H-indole | 1 |
| 5 | 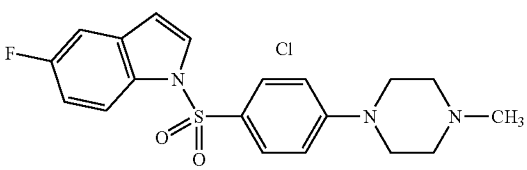 | M + H 374 | 5-Fluoro-1-[4-(4-methyl-piperazin-1-yl)-benzenesulfonyl]-1H-indole | 1 |
| 6 | 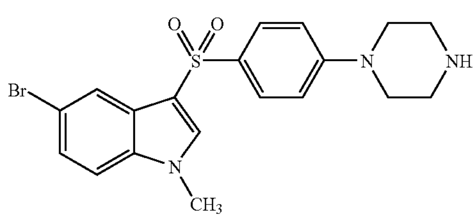 | M + H 435 | 5-Bromo-1-methyl-3-(4-piperazin-1-yl-benzenesulfonyl)-1H-indole | 3 |
| 7 | 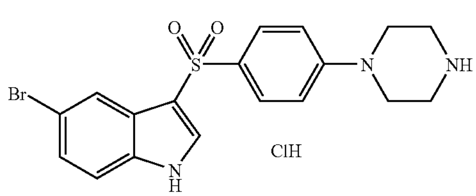 | M + H 421 | 5-Bromo-3-(4-piperazin-1-yl-benzenesulfonyl)-1H-indole | 3 |
| 8 | 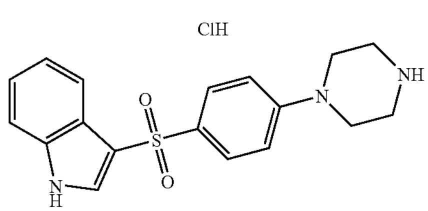 | M + H 342 | 3-(4-Piperazin-1-yl-benzenesulfonyl)-1H-indole | 3 |

TABLE 1-continued

| # | STRUCTURE | M + H or MP ° C. | NAME | Example |
|---|---|---|---|---|
| 9 | 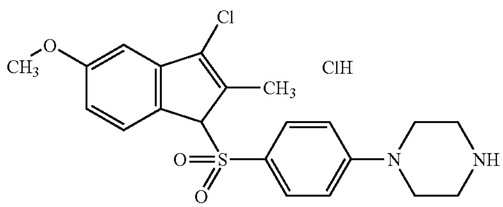 | M + H 420 | 3-Chloro-5-methoxy-2-methyl-1-(4-piperazin-1-yl-benzenesulfonyl)-1H-indole | 1 |
| 10 | 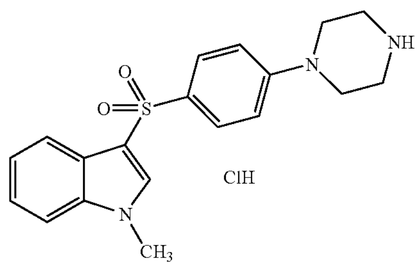 | M + H 356 | 1-Methyl-3-(4-piperazin-1-yl-benzenesulfonyl)-1H-indole | 3 |
| 11 | 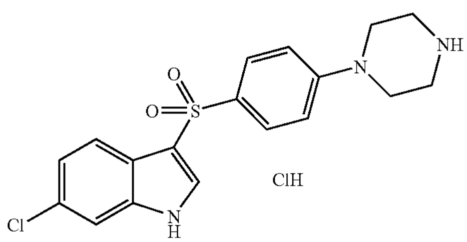 | M + H 376 | 6-Chloro-3-(4-piperazin-1-yl-benzenesulfonyl)-1H-indole | 3 |
| 12 | 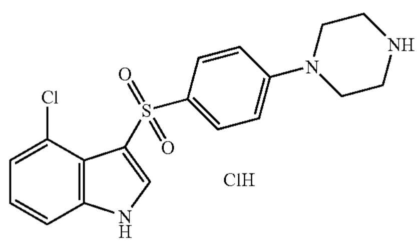 | M + H 376 | 4-Chloro-3-(4-piperazin-1-yl-benzenesulfonyl)-1H-indole | 3 |
| 13 | 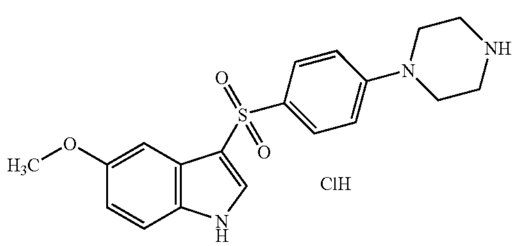 | M + H 372 | 5-Methoxy-3-(4-piperazin-1-yl-benzenesulfonyl)-1H-indole | 3 |
| 14 | 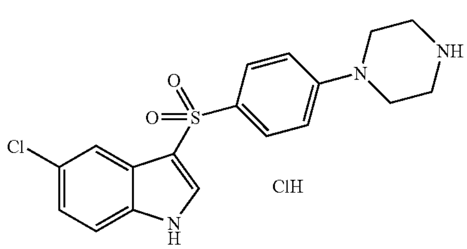 | M + H 376 | 5-Chloro-3-(4-piperazin-1-yl-benzenesulfonyl)-1H-indole | 3 |

TABLE 1-continued

| # | STRUCTURE | M + H or MP ° C. | NAME | Example |
|---|---|---|---|---|
| 15 | 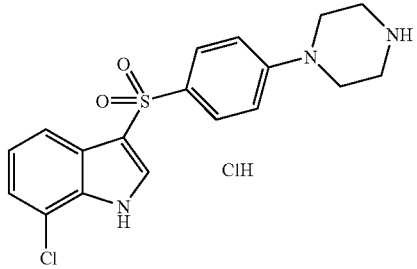 | M + H 376 | 7-Chloro-3-(4-piperazin-1-yl-benzenesulfonyl)-1H-indole | 3 |
| 16 | 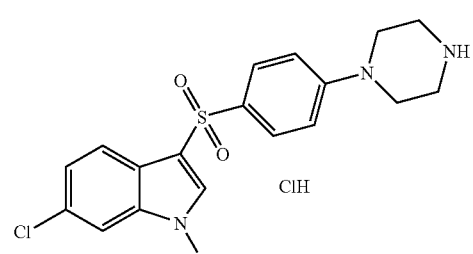 | M + H 422 | 6-Chloro-1-methyl-3-(4-piperazin-1-yl-benzenesulfonyl)-1H-indole | 3 |
| 17 | 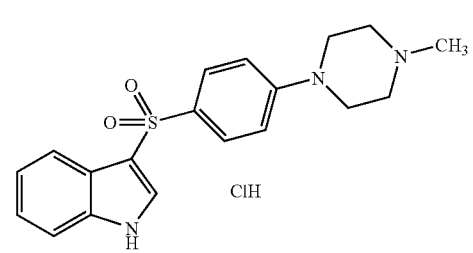 | M + H 356 | 3-[4-(4-Methyl-piperazin-1-yl)-benzenesulfonyl]-1H-indole | 3 |
| 18 | 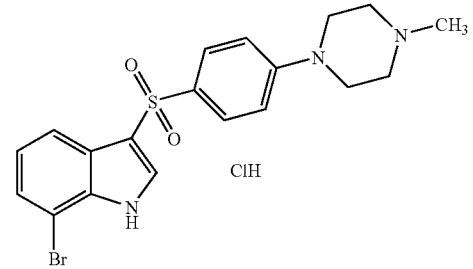 | M + H 435 | 7-Bromo-3-[4-(4-methyl-piperazin-1-yl)-benzenesulfonyl]-1H-indole | 3 |
| 19 | 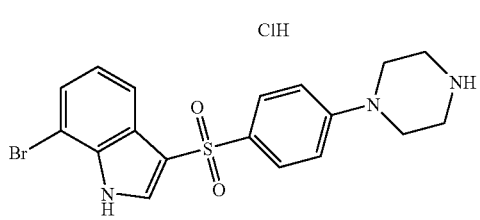 | M + H 421 | 7-Bromo-3-(4-piperazin-1-yl-benzenesulfonyl)-1H-indole | 3 |
| 20 | 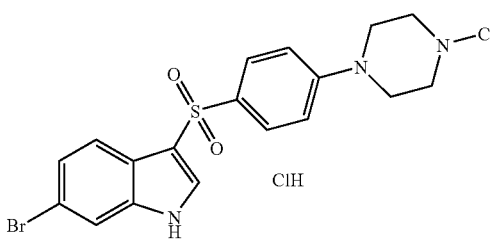 | M + H 435 | 6-Bromo-3-[4-(4-methyl-piperazin-1-yl)-benzenesulfonyl]-1H-indole | 3 |

TABLE 1-continued

| # | STRUCTURE | M + H or MP °C. | NAME | Example |
|---|---|---|---|---|
| 21 | 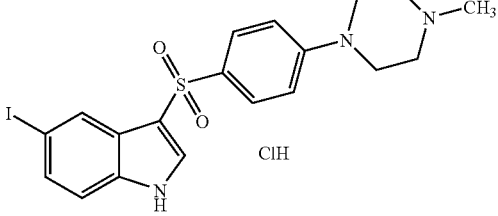 | M + H 482 | 5-Iodo-3-[4-(4-methyl-piperazin-1-yl)-benzenesulfonyl]-1H-indole | 3 |
| 22 | 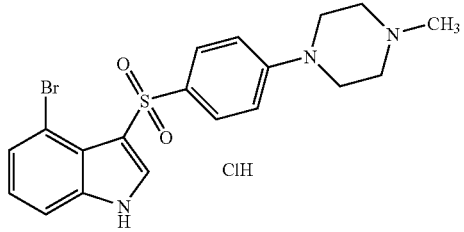 | M + H 435 | 4-Bromo-3-[4-(4-methyl-piperazin-1-yl)-benzenesulfonyl]-1H-indole | 3 |
| 23 | 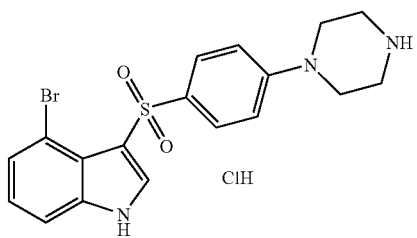 | M + H 421 | 4-Bromo-3-(4-piperazin-1-yl-benzenesulfonyl)-1H-indole | 3 |
| 24 | 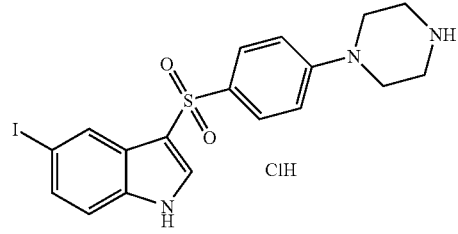 | M + H 468 | 5-Iodo-3-(4-piperazin-1-yl-benzenesulfonyl)-1H-indole | 3 |
| 25 | 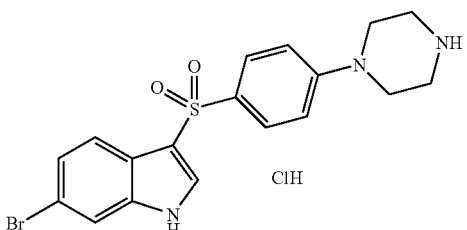 | M + H 421 | 6-Bromo-3-(4-piperazin-1-yl-benzenesulfonyl)-1H-indole | 3 |
| 26 | 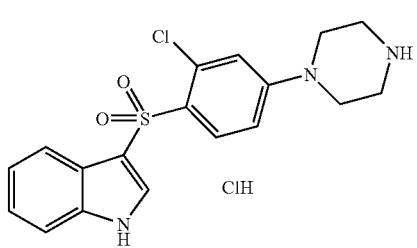 | M + H 376 | 3-(2-Chloro-4-piperazin-1-yl-benzenesulfonyl)-1H-indole | 3 |

TABLE 1-continued

| # | STRUCTURE | M + H or MP °C. | NAME | Example |
|---|---|---|---|---|
| 27 | 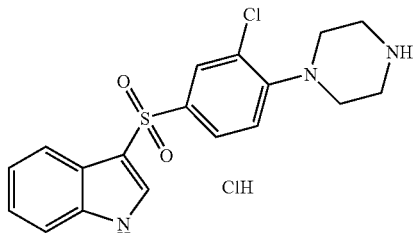 | M + H 376 | 3-(3-Chloro-4-piperazin-1-yl-benzenesulfonyl)-1H-indole | 3 |
| 28 | 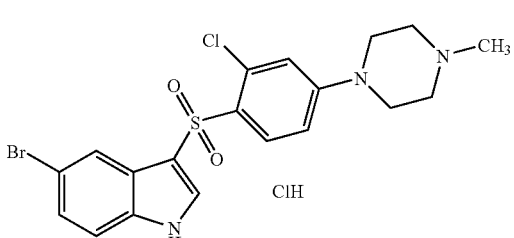 | M + H 468 | 5-Bromo-3-[2-chloro-4-(4-methyl-piperazin-1-yl)-benzenesulfonyl]-1H-indole | 3 |
| 29 | 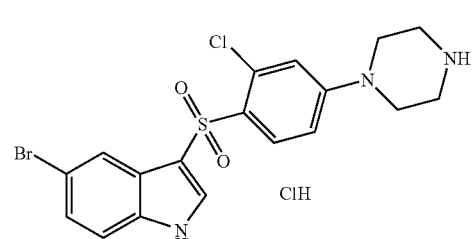 | MP 283–286° | 5-Bromo-3-(2-chloro-4-piperazin-1-yl-benzenesulfonyl)-1H-indole | 3 |
| 30 | 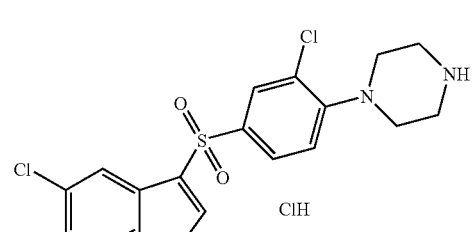 | MP 252–258° | 5-Chloro-3-(3-chloro-4-piperazin-1-yl-benzenesulfonyl)-1H-indole | 3 |
| 31 | 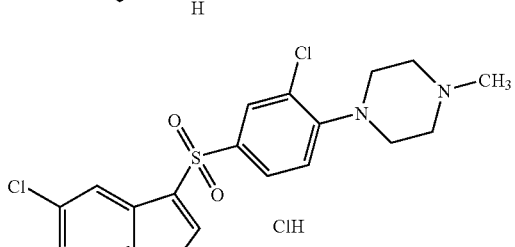 | MP 198–202° | 5-Chloro-3-(3-chloro-4-(4-methyl-piperazin-1-yl)-benzenesulfonyl)-1H-indole | 3 |
| 32 | 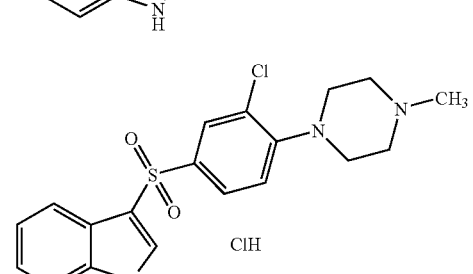 | M + H 390 | 3-(3-chloro-4-(4-methyl-piperazin-1-yl)-benzenesulfonyl)-1H-indole | 3 |

TABLE 1-continued

| # | STRUCTURE | M + H or MP ° C. | NAME | Example |
|---|---|---|---|---|
| 33 | 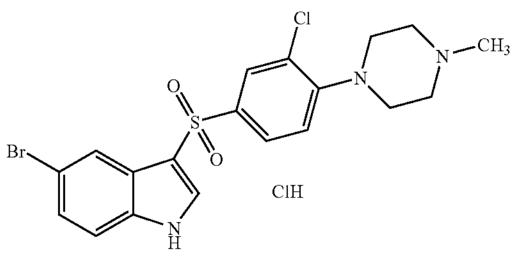 | MP 194–197° | 5-Bromo-3-(3-chloro-4-(4-methyl-piperazin-1-yl)-benzenesulfonyl)-1H-indole | 3 |
| 34 | 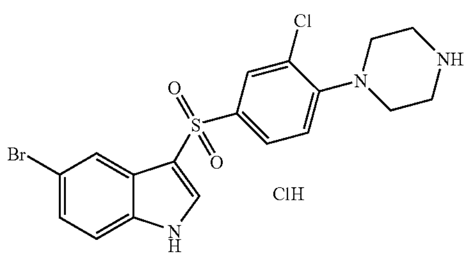 | MP 210–218° | 5-Bromo-3-(3-chloro-4-piperazin-1-yl-benzenesulfonyl)-1H-indole | 3 |
| 35 | 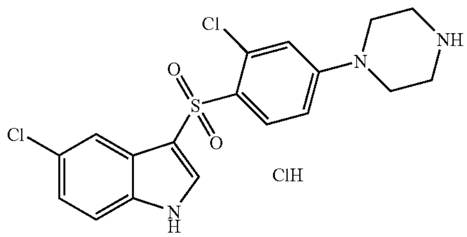 | M + H 410 | 5-Chloro-3-(2-chloro-4-piperazin-1-yl-benzenesulfonyl)-1H-indole | 3 |
| 36 | 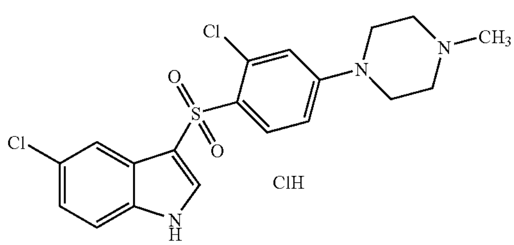 | MP 250° | 5-Chloro-3-(2-chloro-4-(4-methyl-piperazin-1-yl)-benzenesulfonyl)-1H-indole | 3 |
| 37 | 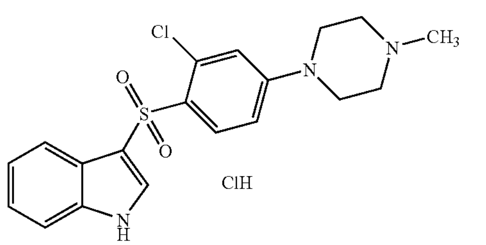 | M + H 390 | 3-(2-chloro-4-(4-methyl-piperazin-1-yl)-benzenesulfonyl)-1H-indole | 3 |
| 38 | 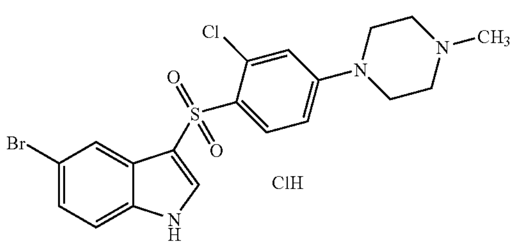 | M + H 468 | 5-Bromo-3-(2-chloro-4-(4-methyl-piperazin-1-yl)-benzenesulfonyl)-1H-indole | 3 |

TABLE 1-continued

| # | STRUCTURE | M + H or MP ° C. | NAME | Example |
|---|-----------|------------------|------|---------|
| 39 | [indole-SO2-phenyl-piperazine structure] | M + H 342 | 2-(4-Piperazin-1-yl-benzenesulfonyl)-1H-indole | 2 |

The invention provides, in another aspect, pharmaceutical compositions comprising at least one Compound of Formula I together with one or more pharmaceutically acceptable carriers, diluents, adjuvants or excipients.

Methods

Yet another aspect of the invention provides methods for treating a central nervous system (CNS) disease state or condition in a subject comprising administering to a subject in need thereof a therapeutically effective amount of at least one Compound of Formula I. The disease state may comprise psychoses, schizophrenia, manic depressions, neurological disorders, memory disorders, attention deficit disorder, Parkinson's disease, amyotrophic lateral sclerosis, Alzheimer's disease and/or Huntington's disease.

Still another aspect of the present invention provides a method for treating a disorder of the gastrointestinal tract in a subject comprising administering to the subject a therapeutically effective amount of a Compound of Formula I.

Another aspect of the present invention provides methods for producing Compounds of Formula I according to the synthetic procedures described below.

Synthesis

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The indole starting materials used herein are commercially available or may be prepared by conventional techniques such as those described by Sundberg, R. J. in *The Chemistry of Indoles*, Academic Press, New York, 1970. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Compounds of Formula III may be prepared as shown in Scheme A wherein X, n, $R^1$, $R^2$, $R^3$, $R^4$, $R^6$, $R^7$, $R^8$ and $R^9$ are as defined herein.

SCHEME A

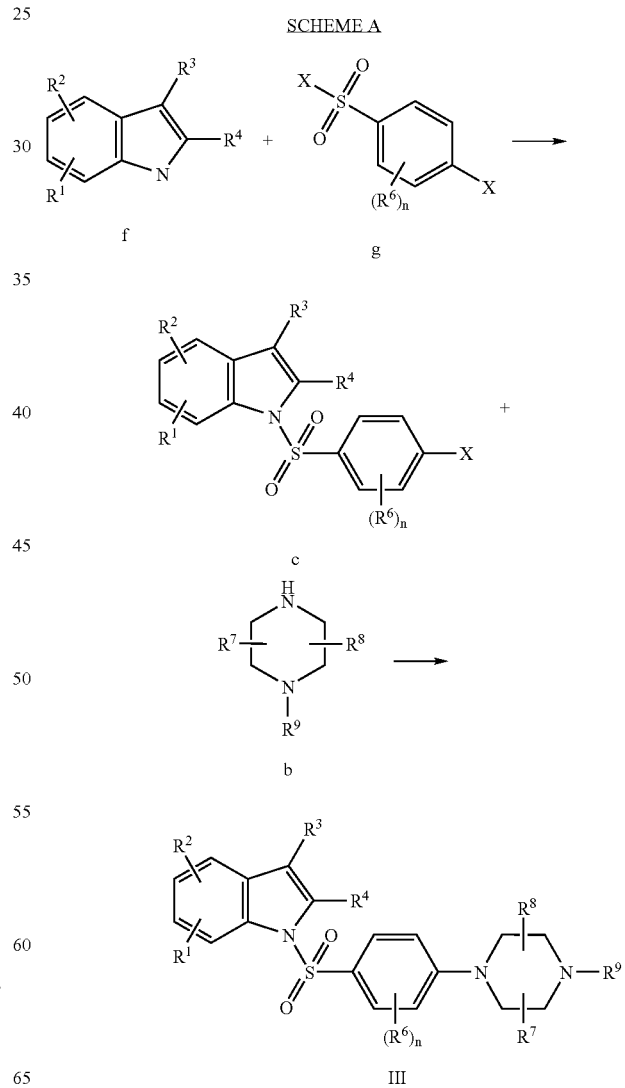

In Scheme A, the 1-(4-halobenzenesulfonyl)-1H-indole c is formed by reaction of the indole compound f under basic conditions with a 4-halophenylsulfonyl halide g having a desired R⁶ substituent(s). The 1-(4-halobenzenesulfonyl)-1H-indole c may then be treated with excess piperazine b in polar aprotic solvent to afford the corresponding 1-(4-piperazin-1-yl-benzenesulfonyl)-1H-indole of Formula III.

Compounds of Formula IV may be prepared according to the procedure shown in Scheme B, wherein X, n, R¹, R², R³, R⁴, R⁶, R⁷, R⁸ and R⁹ are as defined herein.

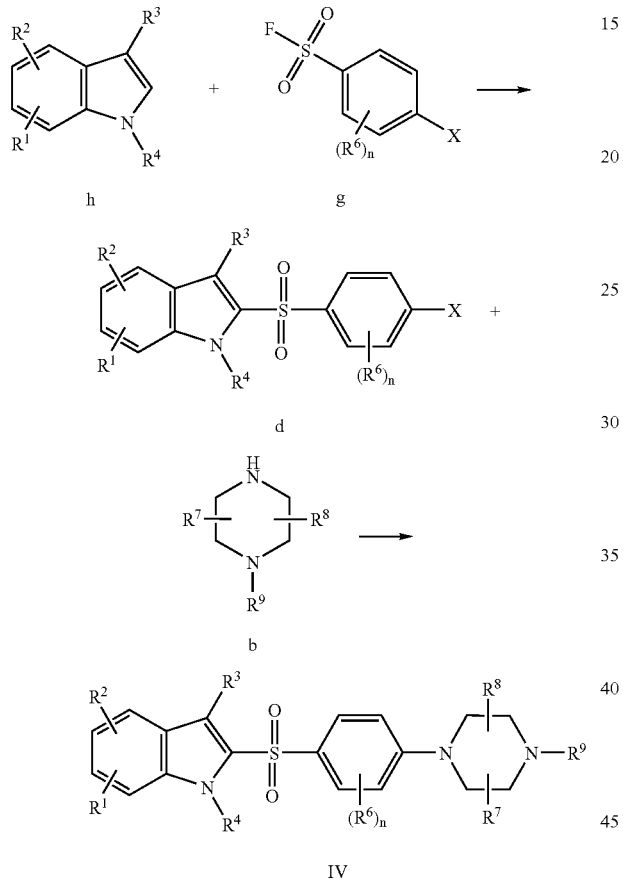

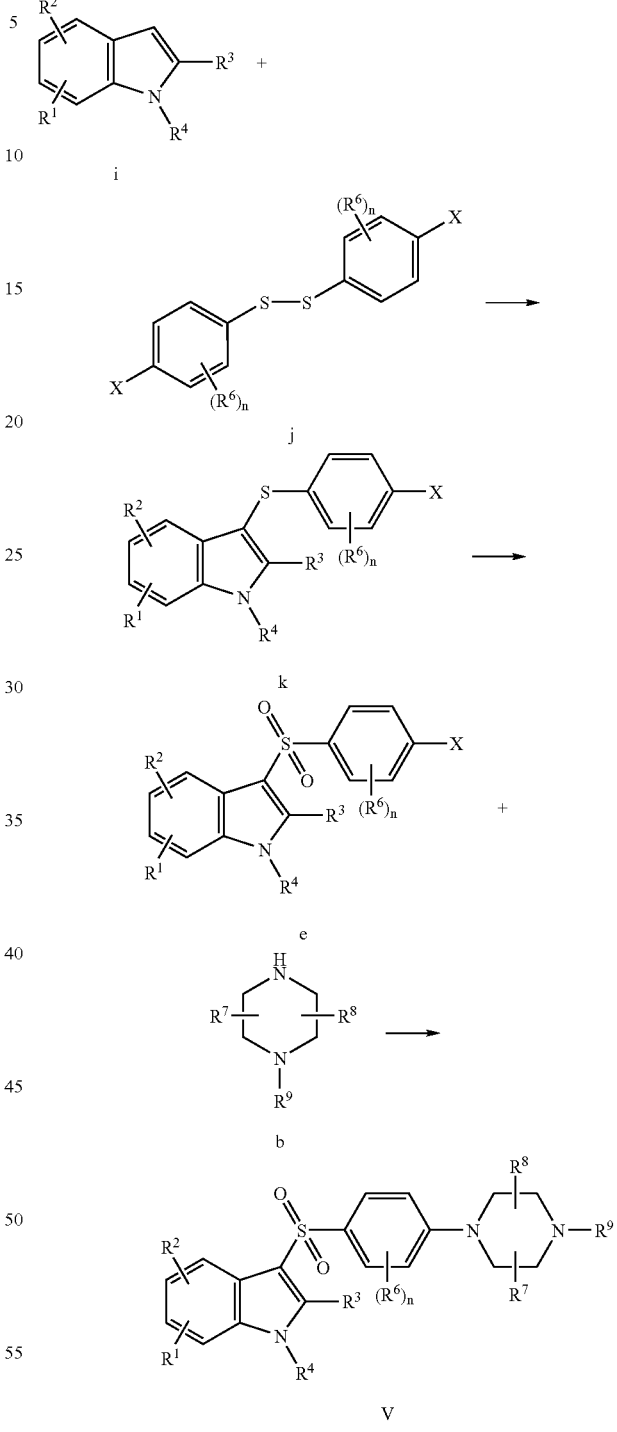

In Scheme B, the indole compound h is treated with an alkyllithium reagent or other strong base under anhydrous polar aprotic conditions and dry ice/acetone temperature to generate the corresponding indole anion (not shown) by deprotonation at the 2-position. Where R⁴ is hydrogen, a suitable removable protecting group may be used to protect the indole nitrogen of compound h. A 4-halophenylsulfonyl fluoride g may then be added directly to the anion of indole compound h to provide the 2-(4-halobenzenesulfonyl)-1H-indole d. Treatment of the 2-(4-halobenzenesulfonyl)-1H-indole d with excess piperazine b can then provide the corresponding 2-(4-piperazin-1-yl-benzenesulfonyl)-1H-indole of Formula IV.

Compounds of Formula V may be prepared according to the procedure shown in Scheme C, wherein X, n, R¹, R², R³, R⁴, R⁶, R⁷, R⁸ and R⁹ again are as defined herein.

In Scheme C, the indole compound i is reacted with a 4-halophenyl disulfide i in the presence of alkalai metal hydride or like strong base under dry polar aprotic conditions to yield the 3-(4-halophenylsulfanyl)-1H-indole compound k. In the procedure of Scheme C, R⁴ of compound i is preferably hydrogen. The compound k may then be treated with a peracid or like oxidizing agent to afford the 3-(4- halobenzenelsulfonyl)-1H-indole compound e. Treatment of the 3-(4-halobenzenesulfonyl)-1H-indole c with excess piperazine b furnishes the 3-(4-piperazin-1-yl-benzenesulfonyl)-1H-indole of Formula V. Where it is desired to have $R^4$ as alkyl in compounds of Formula V, alkylation of the indole nitrogen at the 1-position of the indole ring may be carried out subsequent to formation of the sulfanyl compound k.

Many variations of the above synthetic schemes are possible and will suggest themselves to those skilled in the art. Those skilled in the art will also recognize that stereocenters exist in some compounds of Formula I. Accordingly, the present invention includes all possible stereoisomers and geometric isomers of Formula I, and includes not only racemic compounds but also the optically active isomers as well. When a Compound of Formula I, is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See for example, *Stereochemistry of Carbon Compounds* by E. L. Eliel (McGraw Hill, 1962) and *Tables of Resolving Agents* by S. H. Wilen.

Utility

The compounds of the invention have selective 5-HT6 receptor affinity and as such are expected to be useful in the treatment of certain CNS disorders such as Parkinson's disease, Huntington's disease, anxiety, depression, manic depression, psychosis, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine, and benzodiazepines, schizophrenia, disorders associated with spinal trauma and/or head injury such as hydrocephalus, and other diseases, disorders or conditions mediated by or otherwise associated with the 5-HT6 receptor or other 5-HT receptors. Such compounds are also expected to be of use in the treatment of certain GI (gastrointestinal) disorders such as functional bowel disorder or irritable bowel syndrome (IBS).

Testing

The pharmacology of the compounds of this invention was determined by art recognized procedures. The in vitro techniques for determining the affinities of test compounds at the 5-HT6 receptor in radioligand binding and functional assays are described in Example 5.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous, and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilising agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Example 4.

EXAMPLES

The following preparations and examples are given to enable those skilled in the art to more clearly understand and to practice the present invention. They should not be considered as limiting the scope of the invention, but merely as being illustrative and representative thereof.

Example 1

5-Fluoro-1-(4-piperazin-1-yl-benzenesulfonyl)-1H-indole

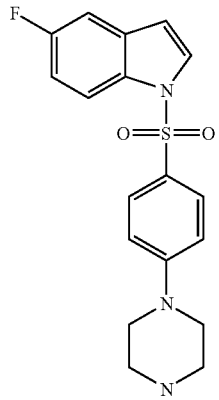

Step 1

1-(4-Chloro-benzenesulfonyl)-5-fluoro-1H-indole

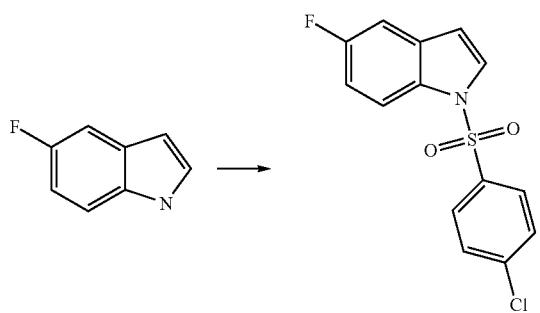

A mixture of 5-fluoroindole (1.0 g, 7.4 mmole), 4-chlorobenzenesulfonyl chloride (1.6 g, 7.6 mmole), tetra-n-butylammonium hydrogen sulfate (0.05 g), 4N sodium hydroxide (5 mL, 20 mmol), and toluene (6 mL) was stirred at room temperature for 15 h. The mixture was diluted with 10 mL water and extracted with 25 mL ethyl acetate. The organic phase was washed with 10 mL water, 10 mL saturated sodium chloride, and then dried (anhydrous magnesium sulfate). The solution was concentrated under reduced pressure. The residue was recrystallized from ethyl ether/hexane to provide 1-(4-Chlorobenzenesulfonyl)-5-fluoro-1H-indole (1.74 g) m.p. 108–109°.

Step 2

5-Fluoro-1-(4-piperazin-1-yl-benzenesulfonyl)-1H-indole

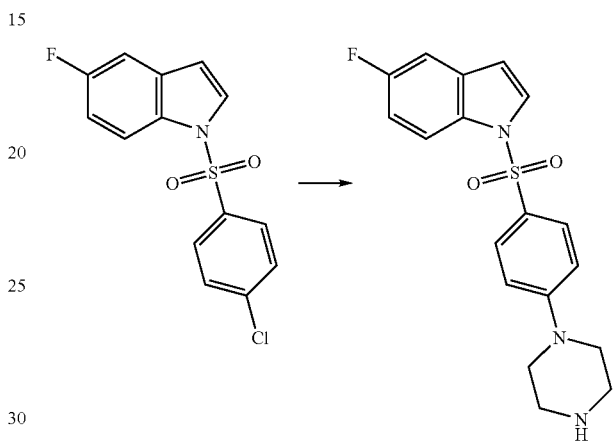

A solution of 1-(4-Chlorobenzenesulfonyl)-5-fluoro-1H-indole (0.210 g, 0.7 mmole) and anhydrous piperazine (0.3 g, 3.4 mmole) in dimethylsulfoxide (3.0 mL) was heated at 100° in a sealed tube for 16 h. The reaction mixture was diluted with 15 mL water and extracted with 20 mL ethyl acetate. The organic phase was washed with three 10 mL portions of water, 10 mL saturated sodium chloride, dried (magnesium sulfate), and concentrated under reduced pressure. The residue was recrystallized from ethyl acetate/hexane to provide the 5-Fluoro-1-(4-piperazin-1-yl-benzenesulfonyl)-1H-indole (0.123 g), m.p. 77–78°.

Similarly following the procedure described above in Example 1, but replacing 5-fluoroindole in Step 1 with other appropriate indoles, the following compounds were prepared:

4-Bromo-1-(4-piperazin-1-yl-benzenesulfonyl)-1H-indole;

5-Methoxy-1-(4-piperazin-1-yl-benzenesulfonyl)-1H-indole;

5-Fluoro-1-[4-(4-methyl-piperazin-1-yl)-benzenesulfonyl]-1H-indole;

3-Chloro-5-methoxy-2-methyl-1-(4-piperazin-1-yl-benzenesulfonyl)-1H-indole; and 1-(4-Piperazin-1-yl-benzenesulfonyl)-1H-indole;

Similarly following the procedure described above in Example 1, but replacing piperazine in Step 2 with N-methylpiperazine, the compound 5-Fluoro-1-[4-(4-methylpiperazin-1-yl)-benzenesulfonyl]-1H-indole was prepared.

Example 2

2-(4-Piperazin-1-yl-benzenesulfonyl)-1H-indole

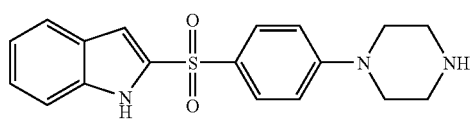

Step 1
2-(4-Fluoro-benzenesulfonyl)-indole-1-carboxylic acid tert-butyl ester

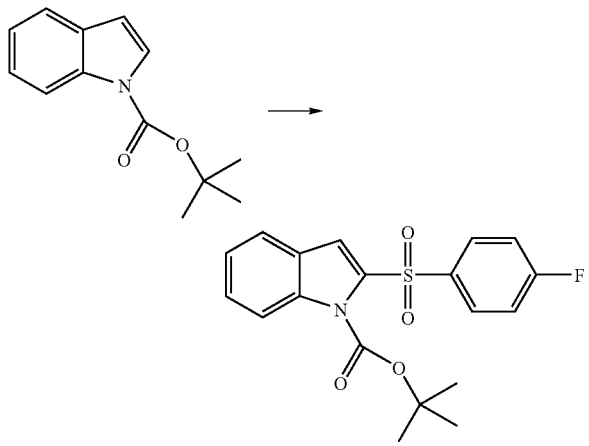

A solution of 1-indole carboxylic acid tert-butyl ester (1.88 g, 8.65 mmol) in 100 mL of anhydrous THF was cooled to −78° C. in a dry ice/acetone bath under an argon gas blanket. A fresh commercial (Aldrich) 1.7 M solution of t-BuLi in pentane (10.2 mL, 17.3 mmol, 2.0 eq) was slowly added to the stirring mixture via syringe. During the addition, the solution turned from a light amber-red color to a dark, orange-burgundy color. After the addition was complete, the reaction mixture was allowed to stir for 45 minutes at −78° C. and then 4-fluorobenzenesulfonyl fluoride was slowly added to the reaction mixture while carefully maintaining an internal temperature of <−65° C. The reaction mixture was kept at −75 to −78° C. for a period of 20 minutes after the addition was complete then was allowed to warm to room temperature, where it remained for 2 h. The reaction mixture was poured into 500 mL of saturated NH₄Cl solution, diluted with 500 mL of EtOAc and mixed well. The pale, amber-orange organic layer was separated, washed with brine and dried over anhydrous magnesium sulfate. Evaporation of the solvent gave a dark amber oil which was silica-gel chromatographed, gradient eluting with 10% EtOAc/Hexane followed by CHCl₃ to give 1.40 g, 3.73 mmol, 43.1% yield of the 2-(4-Fluoro-benzenesulfonyl)-indole-1-carboxylic acid tert-butyl ester as an amber oil which solidified on standing to a pale reddish-tan solid which had a melting point range of 88–93° C.

Step 2
2-(4-Piperazin-1-yl-benzenesulfonyl)-1H-indole

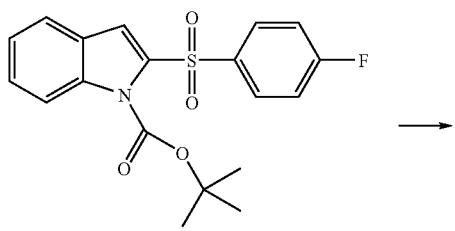

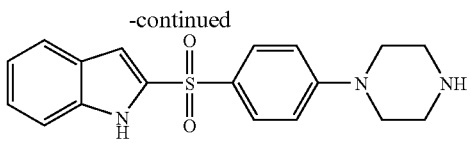

The Boc-protecting group on 0.530 g, 1.41 mmol of the 2-(4-Fluorobenzenesulfonyl)-indole-1-carboxylic acid tert-butyl ester from Step 1 was removed by stirring at room temperature in 3 mL of neat TFA. The reaction mixture turned a light burgundy color while stirring. The TFA was removed by adding 25 mL of toluene and removing the solvent/TFA as an azeotrope. This was repeated and the oily residue was then transferred to a sealed tube using 5 mL of DMSO. Solid piperazine (0.61 g, 7.06 mmol, 5 eq.) was added, the tube was sealed, and the reaction mixture heated at 100° C. (bath temp.) for a period of 16 h. The reaction mixture was allowed to cool to room temperature, diluted with 400 mL of ethyl acetate, then washed sequentially with saturated NaHCO₃ solution, water, brine, and dried over anhydrous magnesium sulfate. Evaporation of the solvent gave an amber glass which was treated with anhydrous diethyl ether. Hexane (25 mL) was added to the solution, causing a small amount of solid to precipitate out of solution. The mixture cooled was to 0° C. in an ice-water bath, followed by vacuum-filtration of the off-white solid. After drying, 0.150 g, 0.44 mmol, 31.1% yield of 2-(4-Piperazin-1-yl-benzenesulfonyl)-1H-indole was obtained, with a melting point range of 246–248.5° C. and M+H of 342.

Example 3

5-Bromo-3-(4-piperazin-1-yl-benzenesulfonyl)-1H-indole

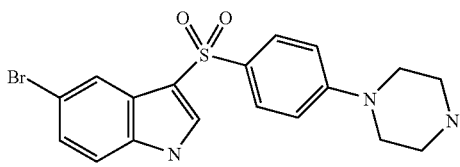

Step 1

5-Bromo-3-(4-fluoro-phenylsulfanyl)-1H-indole

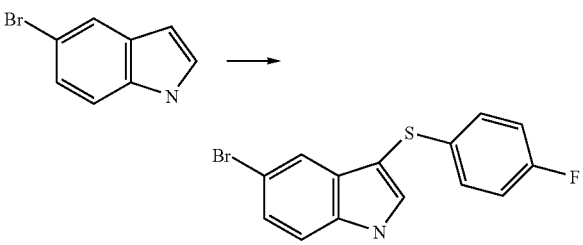

To a stirred mixture of sodium hydride (100%, 0.156 g, 6.5 mmole) in dry N,N-dimethylformamide (12 mL) was added 5-bromoindole (0.98 g, 5 mmole). After 5 minutes 4-fluorophenyl disulfide (1.4 g, 5.5 mmole) was added. The mixture was stirred at room temperature for 48 h. The mixture was diluted with 50 mL water and extracted with 25 mL ethyl ether. The organic phase was washed with 1.5M sodium carbonate (5 mL, 7.5 mmol), 5 mL water, dried (magnesium sulfate), and concentrated under reduced pressure to yield 5-Bromo-3-(4-fluoro-phenylsulfanyl)-1H-indole (1.34 g).

Step 2

5-Bromo-3-(4-fluoro-benzenesulfonyl)-1H-indole

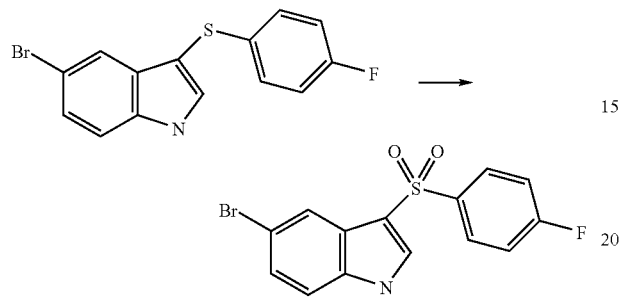

The 5-Bromo-3-(4-fluoro-phenylsulfanyl)-1H-indole (1.34 g, 4.16 mmol) from Step 1 was suspended in formic acid (20 mL). To this was added 30% hydrogen peroxide (0.94 g, 8.3 mmole). The reaction mixture was stirred at room temperature for 1 hour. The mixture was diluted with 80 mL water and extracted with 100 mL ethyl acetate. The organic phase was washed with 1.5M sodium carbonate (20 mL, 30 mmol), dried (magnesium sulfate), and concentrated under reduced pressure. The residue was recrystallized from ether/hexane to provide 5-Bromo-3-(4-fluoro-benzenesulfonyl)-1H-indole (1.4 g, 4.0 mmol), m.p. 163–164°.

Step 3

5-Bromo-3-(4-fluoro-benzenesulfonyl)-1-methyl-1H-indole

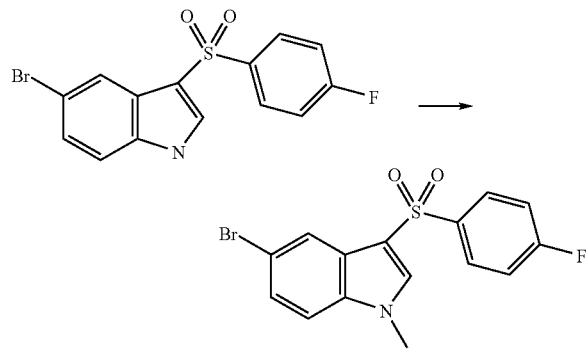

To a stirred solution of 5-bromo-3-(4-fluoro-benzenesulfonyl)-1H-indole (0.315 g, 0.89 mmole) in tetrahydrofuran (4 mL) was added 1M potassium t-butoxide/THF (1.0 mL, 1.0 mmol). After 10 minutes iodomethane (0.16 g, 1.1 mmole) was added. The reaction mixture was stirred at room temperature overnight and then passed through a pad of silica gel (230–400 mesh) eluting with 50% ethyl acetate/hexane. The eluate was concentrated under reduced pressure to provide a residue that was crystallized from ethanol/hexanes to give 0.3 g of 5-Bromo-3-(4-fluoro-benzenesulfonyl)-1-methyl-1H-indole.

Step 4

5-Bromo-1-methyl-3-(4-piperazin-1-yl-benzenesulfonyl)-1H-indole

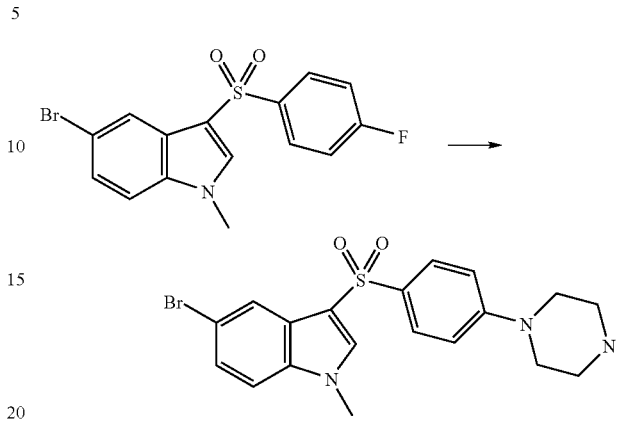

The 5-Bromo-3-(4-fluoro-benzenesulfonyl)-1-methyl-1H-indole (0.30 g, 0.85 mmol) was mixed with piperazine (0.34 g, 4 mmole) and methyl sulfoxide (3 mL). The mixture was heated at 120° C. in a sealed tube for 3 hours. The mixture was diluted with 10 mL water and the resultant precipitate was collected by filtration, washed with water, and recrystallized from chloroform/benzene to provide 5-Bromo-1-methyl-3-(4-piperazin-1yl-benzenesulfonyl)-1H-indole (0.302 g, 0.695 mmol), M+H 436.

Similarly following the procedure described above in Example 3, but replacing 5-bromoindole in Step 1 with other appropriate indoles, the following compounds were prepared:

1-Methyl-3-(4-piperazin-1-yl-benzenesulfonyl)-1H-indole; and

6-Chloro-1-methyl-3-(4-piperazin-1-yl-benzenesulfonyl)-1H-indole.

Similarly following the procedure described above in Example 2, but skipping Step 3 and proceeding directly to Step 4 (and using various appropriate indoles in Step 1), the following compounds were prepared:

5-Bromo-3-(4-piperazin-1-yl-benzenesulfonyl)-1H-indole;

3-(4-Piperazin-1-yl-benzenesulfonyl)-1H-indole;

6-Chloro-3-(4-piperazin-1-yl-benzenesulfonyl)-1H-indole;

4-Chloro-3-(4-piperazin-1-yl-benzenesulfonyl)-1H-indole;

5-Methoxy-3-(4-piperazin-1-yl-benzenesulfonyl)-1H-indole;

5-Chloro-3-(4-piperazin-1-yl-benzenesulfonyl)-1H-indole;

7-Chloro-3-(4-piperazin-1-yl-benzenesulfonyl)-1H-indole;

7-Bromo-3-(4-piperazin-1-yl-benzenesulfonyl)-1H-indole;

4-Bromo-3-(4-piperazin-1-yl-benzenesulfonyl)-1H-indole;

5-Bromo-3-(3-chloro-4-piperazin-1-yl-benzenesulfonyl)-1H-indole;

5-Iodo-3-(4-piperazin-1-yl-benzenesulfonyl)-1H-indole; and

6-Bromo-3-(4-piperazin-1-yl-benzenesulfonyl)-1H-indole.

Similarly following the procedure described above in Example 3, but skipping Step 3 and proceeding directly to Step 4, and replacing piperazine with N-methylpiperazine (using various appropriate indoles in Step 1), the following compounds were prepared:

3-[4-(4-methyl-piperazin-1-yl)-benzenesulfonyl]-1H-indole;

7-Bromo-3-[4-(4-methyl-piperazin-1-yl)-benzenesulfonyl]-1H-indole;

6-Bromo-3-[4-(4-methyl-piperazin-1-yl)-benzenesulfonyl]-1H-indole;

5-Iodo-3-[4-(4-methyl-piperazin-1-yl)-benzenesulfonyl]-1H-indole; and

4-Bromo-3-[4-(4-methyl-piperazin-1-yl)-benzenesulfonyl]-1H-indole.

Similarly following the procedure described above in Example 3, skipping Step 3 and proceeding directly to Step 4, using various appropriate indoles in Step 1, and replacing 4-fluorophenyl disulfide in Step 1 with the appropriate disulfides, the following compounds were prepared:

5-Chloro-3-(3-chloro-4-piperazin-1-yl-benzenesulfonyl)-1H-indole;

5-Chloro-3-(2-chloro-4-piperazin-1-yl-benzenesulfonyl)-1H-indole;

3-(2-chloro-4-piperazin-1-yl-benzenesulfonyl)-1H-indole;

3-(3-chloro-4-piperazin-1-yl-benzenesulfonyl)-1H-indole; and

5-Bromo-3-(2-chloro-4-piperazin-1-yl-benzenesulfonyl)-1H-indole.

Similarly following the procedure described above in Example 3, skipping Step 3 and proceeding directly to Step 4 (and replacing piperazine with N-methylpiperazine), using various appropriate indoles in Step 1, and replacing 4-fluorophenyl disulfide in Step 1 with the appropriate phenyl disulfides, the following compounds were prepared:

5-Bromo-3-[2-chloro-4-(4-methyl-piperazin-1-yl)-benzenesulfonyl]-1H-indole;

5-Chloro-3-(3-chloro-4-(4-methyl-piperazin-1-yl)-benzenesulfonyl)-1H-indole;

5-Bromo-3-(3-chloro-4-(4-methyl-piperazin-1-yl)-benzenesulfonyl)-1H-indole;

3-(3-chloro-4-(4-methyl-piperazin-1-yl)-benzenesulfonyl)-1H-indole;

5-Chloro-3-(2-chloro-4-(4-methyl-piperazin-1-yl)-benzenesulfonyl)-1H-indole; and 3-(2-chloro-4-(4-methyl-piperazin-1-yl)-benzenesulfonyl)-1H-indole.

Example 4

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 5

Radioligand Binding Studies

The binding activity of compounds of this invention in vitro was determined as follows.

Duplicate determinations of ligand affinity are made by competing for binding of [3H]LSD in cell membranes derived from HEK293 cells stably expressing recombinant human 5-HT6 receptor.

All determinations are made in assay buffer containing 50 mM Tris-HCl, 10 mM MgSO4, 0.5 mM EDTA, 1 mM ascorbic acid, pH 7.4 at 37° C., in a 250 microliter reaction volume. Assay tubes containing [3H] LSD (5 nM), competing ligand, and membrane are incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [3H] LSD is determined as radioactive counts per minute using Packard TopCount.

Displacement of [3H]LSD from the binding sites was quantified by fitting concentration-binding data to a 4-parameter logistic equation:

$$binding = basal + \left( \frac{Bmax - basal}{1 + 10^{-Hill(\log[ligand] - \log IC_{50})}} \right)$$

where Hill is the Hill slope, [ligand] is the concentration of competing radioligand and IC50 is the concentration of radioligand producing half-maximal specific binding of radioligand. The specific binding window is the difference between the Bmax and the basal parameters.

Using the procedure of this Example, Compounds of Formula I were tested and found to be selective 5-HT6 antagonists.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

The invention claimed is:

1. A compound of the formula:

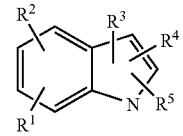

wherein:

$R^1$ and $R^2$ each independently is hydrogen, alkyl, aryl, halo, nitro, amino, cyano, alkoxy, hydroxy, aryloxy, alkylthio, arylthio, thiol, carbonylamino, aminocarbonyl, or haloalkyl;

$R^3$ and $R^4$ each independently is hydrogen, halo, alkyl, aryl, or arylalkyl;

$R^5$ is:

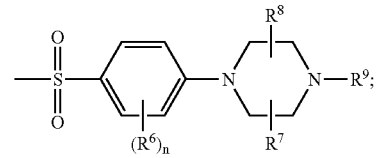

n is 0 to 4;

$R^6$ in each independent occurrence is hydrogen, alkyl, alkoxy, or halo;

$R^7$ and $R^8$ each independently is hydrogen or alkyl; and $R^9$ is hydrogen, alkyl, or arylalkyl;

or an individual isomer, a racemic or non racemic mixture of isomers, a prodrug, or a pharmaceutically acceptable salt or solvate thereof.

2. The compound of claim 1, wherein $R^3$ and $R^4$ each independently is hydrogen, halo or alkyl.

3. The compound of claim 1, wherein $R^1$ and $R^2$ each independently is hydrogen, halo, or alkoxy.

4. The compound of claim 1, wherein n is 1 and wherein $R^6$ is hydrogen or halo.

5. The compound of claim 1, wherein $R^7$ and $R^8$ are hydrogen.

6. The compound of claim 1, wherein $R^9$ is hydrogen or alkyl.

7. The compound of claim 1, wherein:

$R^1$ and $R^2$ each independently is hydrogen, halo, or alkoxy;

$R^3$ and $R^4$ each independently is hydrogen, halo or alkyl;

n is 1 and $R^6$ is hydrogen or halo;

$R^7$ and $R^8$ are hydrogen; and $R^9$ is hydrogen or alkyl.

8. The compound of claim 7, wherein said compound has the formula:

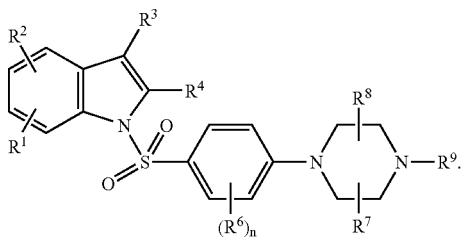

9. The compound of claim 7, wherein said compound has the formula:

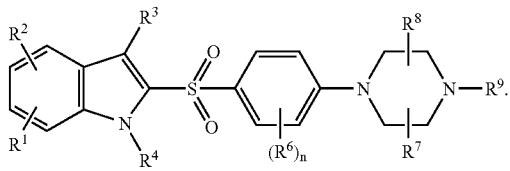

10. The compound of claim 7, wherein said compound has the formula:

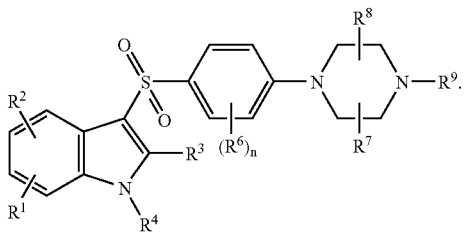

11. The compound of claim 8, wherein one of $R^1$ and $R^2$ is halo and the other is hydrogen.

12. The compound of claim 10, wherein one of $R^1$ and $R^2$ is halo and the other is hydrogen.

13. The compound of claim 12, wherein n is 1 and $R^6$ is halo.

14. The compound of claim 12, wherein n is 0.

15. The compound of claim 10, wherein $R^1$ and $R^2$ are hydrogen.

16. The compound of claim 15, wherein n is 1 and $R^6$ is halo.

17. The compound of claim 15, wherein n is 0.

18. The compound of claim 12, wherein $R^9$ is hydrogen.

19. The compound of claim 12, wherein $R^9$ is methyl.

20. The compound of claim 13, wherein $R^9$ is hydrogen.

21. The compound of claim 13, wherein $R^9$ is methyl.

22. The compound of claim 14, wherein $R^9$ is hydrogen.

23. The compound of claim 14, wherein $R^9$ is methyl.

24. The compound of claim 15, wherein $R^9$ is hydrogen.

25. The compound of claim 15, wherein $R^9$ is methyl.

26. The compound of claim 16, wherein $R^9$ is hydrogen.

27. The compound of claim 16, wherein $R^9$ is methyl.

28. The compound of claim 17, wherein $R^9$ is hydrogen.

29. The compound of claim 17, wherein $R^9$ is methyl.

30. A pharmaceutical composition comprising, comprising a compound of claim 1 together with a pharmaceutically acceptable carrier.

31. A method for treating a central nervous system disease state in a subject, said disease state selected from the group consisting of schizophrenia, depression and enhancement of cognitive memory said method comprising administering to said subject a therapeutically effective amount of a compound of claim 1.

32. A method for producing a compound of claim 1, comprising contacting a 4-halobenzenesulfonyl-indole of the formula:

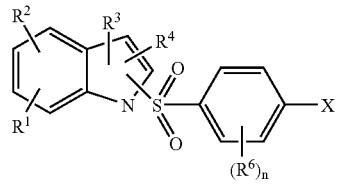

with a piperazine of the formula:

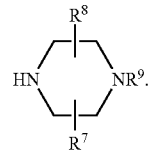

to produce a compound of the formula:

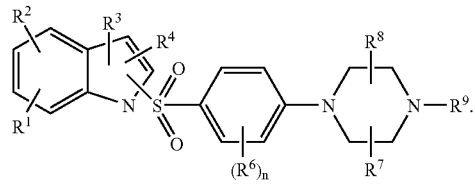

* * * * *